(12) United States Patent
Stihl

(10) Patent No.: US 6,189,422 B1
(45) Date of Patent: Feb. 20, 2001

(54) SCREWDRIVER

(75) Inventor: Ewald Stihl, Geisingen (DE)

(73) Assignee: Karl Storz GmbH & Co. KG (DE)

( * ) Notice: Under 35 U.S.C. 154(b), the term of this patent shall be extended for 0 days.

(21) Appl. No.: 09/524,935

(22) Filed: Mar. 14, 2000

Related U.S. Application Data

(63) Continuation of application No. PCT/EP99/05076, filed on Jul. 16, 1999.

(30) Foreign Application Priority Data

Jul. 17, 1998 (DE) .............................................. 198 32 303

(51) Int. Cl.[7] ..................................................... B25B 23/10
(52) U.S. Cl. ............................... 81/452; 81/453; 81/455; 606/104
(58) Field of Search .............................. 81/452–455, 457; 606/104

(56) References Cited

U.S. PATENT DOCUMENTS

| | | | |
|---|---|---|---|
| 2,954,809 | * | 10/1960 | Loewy ..................................... 81/452 |
| 4,363,250 | * | 12/1982 | Suga ........................................ 81/455 |
| 4,478,113 | * | 10/1984 | Berneiser ........................... 81/455 X |
| 4,581,963 | * | 4/1986 | Kim ........................................ 81/452 |
| 4,763,548 | * | 8/1988 | Leibinger et al. ...................... 81/453 |
| 5,649,931 | * | 7/1997 | Bryant et al. ....................... 81/453 X |
| 5,667,513 | * | 9/1997 | Torrie et al. ........................ 81/453 X |

\* cited by examiner

*Primary Examiner*—James G. Smith
(74) *Attorney, Agent, or Firm*—St.Onge Steward Johnston & Reens LLC

(57) ABSTRACT

A screwdriver for introducing and screwing a screw into the human or animal body and/or for unscrewing and removing a screw from the human or animal body has a handle and a shaft whose front end has a blade that can be brought into engagement with a screw head of the screw for screwing the screw. The screwdriver furthermore has a retention device for retaining the screw on the blade. The retention device has an inner tubular shaft which surrounds the shaft and has at the distal end a clamping gripper preloaded into its open position, and an outer tubular shaft surrounding the inner tubular shaft. Arranged on the handle is an actuation device for the inner tubular shaft and outer tubular shaft that is movable from a first position into a second position, as a result of which the opened clamping gripper is displaced over the blade out of a pulled-back position, and the actuation device being movable out of the second position into a third position, as a result of which the outer tubular shaft is displaced relative to the inner tubular shaft over the clamping gripper in order to close the latter, and vice versa.

20 Claims, 5 Drawing Sheets

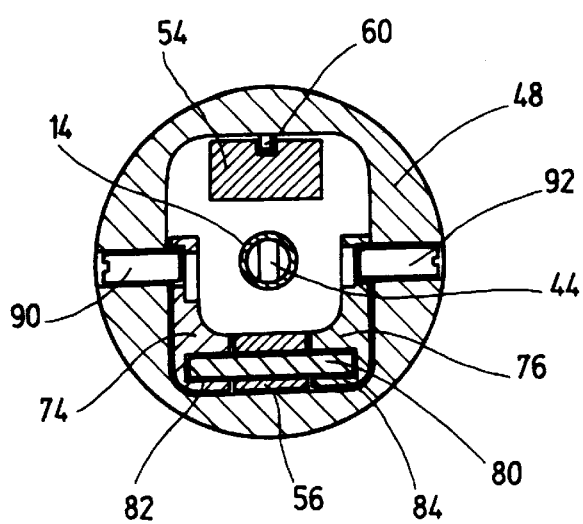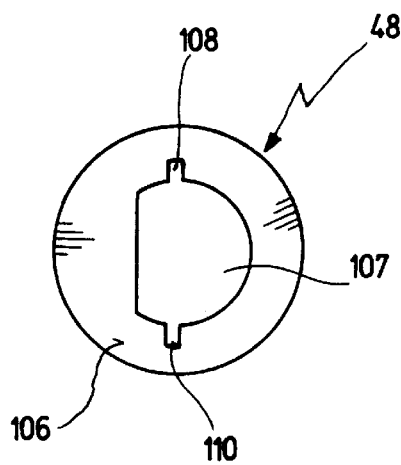
Fig. 6
Fig. 7
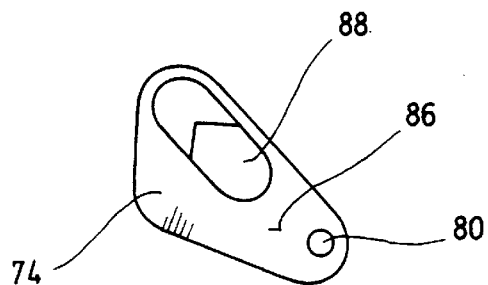
Fig. 8
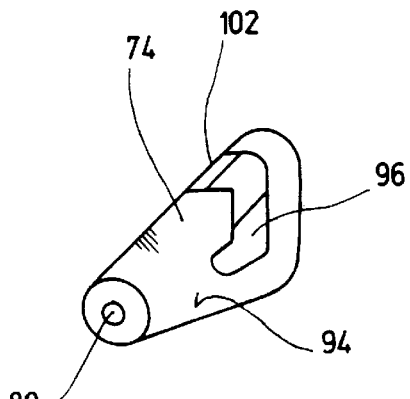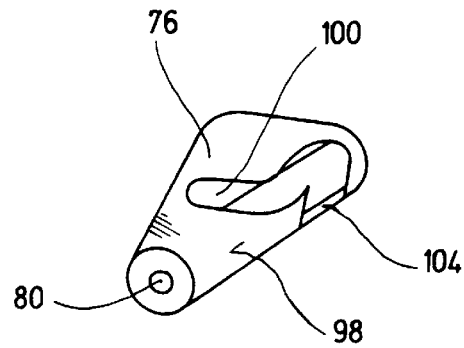
Fig. 9
Fig. 10

SCREWDRIVER

CROSS REFERENCE TO PENDING APPLICATION

The application is a continuation of pending International Patent Application PCT/EP99/05076 filed on Jul. 16, 1999.

BACKGROUND OF THE INVENTION

The present invention relates to a screwdriver for introducing and screwing a screw into the human or animal body and/or for unscrewing and removing a screw from the human body.

A screwdriver of this kind for medical purposes is known from DE 35 39 502 C1.

In the area of medical surgery, screwdrivers are used to screw bond screws into bones in the human or animal body and to remove them again. The problem frequently arises in this context that the surgical field into which the screw is to be introduced is difficult to access from outside, so that it is not possible to bring the screw to the target location by hand and hold it there so the screw can then be accurately and securely screwed in, unless a large opening in the body is created for that purpose in order to expose the surgical field, or a second incision is created into which an instrument for guiding and holding the screw can be introduced.

One special application in surgery is laparoscopic spinal column surgery, in which a bone screw, or several bond screws in succession, is or are brought through the abdominal cavity through a surgical opening in the abdominal wall to the spinal column and screwed into the latter. A screwdriver having a correspondingly elongated shaft is necessary for this procedure. Since it is desirable to perform such an operation in minimally invasive fashion, i.e. from outside through the smallest possible incision in the abdominal wall, there exists a need for a screwdriver with which the screw can not only be screwed in, but also first reliably introduced through the abdominal cavity to the spinal column without having the screw fall off the screwdriver during insertion. The screw must also be capable of being held by the screwdriver so securely that at the target location at which the screw is to be screwed in, it can be put in place without tilting to the side when pressure is exerted on the screw. It should moreover be possible, in one working step, not only to set the screw in place but also to screw it completely into the bone, without having the retention device interfere with complete insertion of the screw.

The screwdriver known from the aforementioned DE 35 39 502 C1 for introducing and screwing in a bone screw has a handle as well as a shaft whose front end has a head which can be brought into engagement with a screw head of the screw in order to screw in and unscrew the screw. The screwdriver furthermore has a retention device for retaining the screw on the shaft, the retention device having an inner tubular shaft which surrounds the shaft and has at the front end a clamping gripper preloaded into its open position, and an outer tubular shaft surrounding the inner tubular shaft. The screwdriver furthermore has an actuation device for the inner tubular shaft and outer tubular shaft which can be moved from a first position into a second position, thereby displacing the clamping gripper over the head from a pulled-back position, the actuation device being movable from the second position into a third position which causes the outer tubular shaft to be displaced relative to the inner tubular shaft over the clamping gripper in order to close the latter, and vice versa. The longitudinal movement of the outer tubular shaft with respect to the inner tubular shaft is limited in each case, in the direction away from the tool, by stops.

With this known screwdriver, the inner tubular shaft, the outer tubular shaft, and the shaft itself can be removed from the handle, for which purpose a coupling is provided between the tool shaft and the handle. The fact that the known screwdriver can be disassembled means that the screwdriver can be sterilized, so that the known screwdriver also meets the requirements for easy cleaning that always apply to medical instruments.

It is, however, disadvantageous in terms of the design and handling capabilities of this known screwdriver that in order to remove the tool shaft, an actuation device separate from the actuation device for the retention device is provided. This second actuation device for disassembling the instrument comprises a sliding sleeve that is arranged between the handle and the actuation device for the retention device. The handling of the known screwdriver is complicated by the fact that because of the actuation device for disassembling the instrument, the actuation device for the retention device is located far away, thus making one-hand handling impossible or at least difficult.

DE 38 4 749 A1 furthermore discloses a screwdriver having a retention device for bone screws. With this screwdriver, no mention is made of the possibility for disassembly into handle and shaft parts.

CH Patent 369 416 also discloses a screwdriver having a gripper for retaining a screw, in which the gripper sleeve, slid onto the screwdriver loosely on the shaft, possesses inwardly protruding holding means, engaging the former and imparting a flexible braking effect, in such a way that the gripper sleeve, when displaced, automatically holds itself on the screwdriver shaft and, to allow disassembly of the latter, the gripper sleeve can be completely pulled off the screwdriver shaft as a result of its loose arrangement. With this known screwdriver, the retention device therefore cannot be immobilized on the handle.

U.S. Pat. No. 2,370,407 discloses a screwdriver having a retention device for a screw that also has an inner tubular shaft with a clamping gripper and an outer tubular shaft which can be displaced axially on the inner tubular shaft in order to close and open the clamping gripper. A nut that is immovably joined to the outer tubular shaft and is in threaded engagement with the inner tubular shaft is provided as an actuation device for displacing the outer shaft relative to the inner tubular shaft. The inner tubular shaft and outer tubular shaft are not immobilized on the handle while the screwdriver is in operation.

Lastly, DE 37 14 994 C1 discloses a screwdriver having a screw holding apparatus, in which the screw holding apparatus can be screwed as a part onto threads on the shaft of a screwdriver. For that purpose, the screw holding apparatus comprises a retaining jaw sleeve on which the sleeve of a detent bushing sleeve is arranged. The detent bushing, which can be screwed onto the sleeve, is rotatably joined to an adjusting screw. For assembly, firstly the retaining jaw sleeve is inserted from one side into a slide bushing while compressing the detent tooth clamps, once the sleeve has previously been slid on. The detent bushing is then introduced into the slide bushing from the other side, and is thread-joined to the sleeve. With this known screwdriver, the disassembly capability is achieved with a complex design. Handling in order to disassemble and assemble the screwdriver is also complicated.

It is therefore one object of the present invention to develop a screwdriver of the kind cited initially in such a way that, with a configuration of simple design, both actuation of the retention device and disassembly and assembly of the screwdriver are easy.

SUMMARY OF THE INVENTION

According to the present invention this object is achieved by a screwdriver for introducing and screwing a screw into the human or animal body and/or for unscrewing and removing a screw from the human or animal body, comprising:

- a handle;
- a shaft connected to said handle, said shaft having a head at a front end of said shaft that can be brought into engagement with a screw head of a screw for screwing said screw in and out;
- a retention device for retaining said screw on said shaft, said retention device having an inner tubular shaft surrounding said shaft and having a clamping gripper at a front end of said inner tubular shaft, said clamping gripper being preloaded into an open position, said retention device further having an outer tubular shaft surrounding said inner tubular shaft;
- an actuation device for said inner tubular shaft and said outer tubular shaft, said actuation device being movable from a first position into a second position, as a result of which said clamping gripper is displaced over said head from a pulled-back position, and said actuation device being movable out of said second position into a third position, as a result of which said outer tubular shaft is displaced relative to said inner tubular shaft over said clamping gripper in order to close the latter, and vice versa, wherein

- at least one of said inner tubular shaft and said outer tubular shaft is joined removably to said handle, and
- said actuation device is arranged on said handle and is movable into a fourth position in which said at least one of said inner tubular shaft and said outer tubular shaft is removable from said handle, and
- said at least one of said inner tubular shaft and said outer tubular shaft is fixed on said handle by moving said actuation device from said fourth position into said first position.

According to the present invention, not only can the functions of opening and closing the clamping gripper and sliding the clamping gripper forward and backward be performed with one hand using the actuation device provided on the handle, but disassembly of the screwdriver into its individual parts is also brought about by operating the same actuation device, thus simplifying the handling of the screwdriver according to the present invention. With the actuation device in the first, second, and third positions, the inner tubular shaft and the outer tubular shaft are always immovably joined to the handle. The fact that the actuation device additionally has a fourth disassembly position makes it possible for the actuation device for the retention device to be arranged directly on the handle and thus conveniently operably with one hand, since no additional actuation device is necessary for disassembly.

In a preferred embodiment, the inner tubular shaft and the outer tubular shaft are together axially displaced by moving the actuation device between the first and the second position.

In a further preferred embodiment, the inner tubular shaft and/or the outer tubular shaft is/are joined to the handle by a quick-release connection.

This feature has the further advantage that handling of the screwdriver according to the present invention is substantially simplified during its disassembly as well, and that after it has been disassembled the screwdriver can be reassembled in an easily handled manner for re-use.

It is preferred in this context that the actuation device be movable into the fourth position only after an interlock has been disengaged.

The advantage of this feature is that the actuation device is not inadvertently brought into the disassembly position during a surgical procedure, thus improving the operating reliability of the screwdriver.

In further preferred embodiments, the interlock can be disengaged by way of a pushbutton or by rotating the actuation device.

These features represent technically simple and easily handled embodiments of the interlock.

In a further preferred embodiment, the actuation device snaps into the first, second, third, and/or optionally fourth position.

The particular advantage of this feature is that because the actuation device snaps into the respective position, the surgeon can perceive the operating position of the clamping gripper, its closed or open position, and its axial position even without checking visually. This is advantageous in particular when releasing the clamping gripper from the screw head before completely screwing the screw into the bone, when the actuation device is moved out of the third position (in which the screw is retained on the screwdriver) into the first position (in which the clamping gripper is pulled back behind the screw head so that the screw head is completely exposed). A further advantage of snapping into the third position of the actuation device, in which the clamping gripper is closed, is that even if the actuation device is released, it remains in the third position so that the clamping gripper does not unintentionally open.

It is preferred in this context if the actuation device has ball catches for the first, second, third, and/or optionally fourth position.

Ball catches represent a reliably operating, easily implemented possibility for the snap-locking capability of the actuation device. In addition, ball catches have the advantage of being smoothly operating, so that the actuation device can be moved out of the snap positions without great exertion and essentially without jerking.

In a further preferred embodiment, the actuation device has at least one slider that is arranged in axially displaceable fashion on the handle.

Since the functions of the clamping gripper, namely axial displacement and opening and closing, are executed by way of axial movements of the inner tubular shaft and the outer tubular shaft, a slider has the advantage, for example over a rotatable actuation device, that the transfer of motion from the actuation device to the inner tubular shaft or outer tubular shaft is easy to implement mechanically. A further advantage is the fact that an axial slider makes possible a direct transfer of motion to the inner or outer tubular shaft, so that the movement travel of the slider is approximately equal to the movement travel of the inner tubular shaft, so that the surgeon can more easily become accustomed to the handling of the screwdriver according to the present invention.

It is preferred in this context if the slider is arranged at the front end of the handle.

This feature results in a particularly easy-to-operate screwdriver, since the surgeon can conveniently operate the slider of the actuation device, for example with the thumb and index finger of the same hand with which he or she is holding the screwdriver handle, in order to actuate the clamping gripper.

In a further preferred embodiment, the actuation device has at least one first control element that has on its inner side a groove configured as a cam into which a pin arranged at the rear end of the outer tubular shaft engages, the control element being mounted on the handle pivotably about a pivot axis running perpendicular to the longitudinal direction of the shaft, and the slider having a pin that engages into a guide groove on the outer side of the control element, so that by axial displacement of the slider, the control element is pivoted and the outer tubular shaft is thereby displaced.

The advantage of this embodiment is that an axial displacement of the slider is transferred to the outer tubular shaft by way of the control element, for the functions of closing and opening the clamping gripper, in a mechanically simple and kinematically favorable fashion. With this configuration, the displacement of the inner tubular shaft can be brought about by the fact that the outer tubular shaft entrains the inner tubular shaft as it is displaced axially. For closing and opening the clamping gripper and for the relative movement provided therefor between outer tubular shaft and inner tubular shaft, a stop can be provided by way of which the inner tubular shaft remains stationary when its maximum forward position is reached, and only the outer tubular shaft is axially displaced farther.

In a farther preferred embodiment, the actuation device has at least one second control element that has on its inner side a groove, configured as a cam, into which engages a pin arranged at the rear end of the inner tubular shaft, the control element being mounted on the handle pivotably about a pivot axis running perpendicular to the longitudinal direction of the shaft, and the slider having a pin which engages into a guide groove on the outer side of the control element so that by axial displacement of the slider, the control element is pivoted and the inner tubular shaft is thereby displaced.

This feature has the advantage, in combination with the previous configuration, of creating for the inner tubular shaft a control system independent of the control system of the outer tubular shaft, thus ensuring that when the actuation device is actuated, the functions of closing and opening the clamping gripper, and pulling the clamping gripper back and pushing it forward, are performed without interference.

It is preferred in this context if the groove of the first control element and the groove of the second control element are open at their front ends, and if the pin of the outer tubular shaft and the pin of the inner tubular shaft can enter the groove and emerge from it axially when the actuation device is in its fourth position, and if the pin of the inner tubular shaft and the pin of the outer tubular shaft are captured in the groove as soon as the actuation device has been moved into the first position.

This feature has the further advantage that the inner tubular shaft and outer tubular shaft automatically come into engagement with the actuation device by being pushed together with the handle, and can be immobilized on the handle and unlocked again by way of an easily handled movement of the actuation device. This configuration creates a simple and mechanically advantageous quick-release connection between the inner tubular shaft and outer tubular shaft on the one hand, and the handle on the other hand.

In a further preferred embodiment, a distal end face of the slider has a non-round opening through which the outer tubular shaft is passed, a rear end segment of the outer tubular shaft having a corresponding complementary peripheral shape.

The advantage of this feature is that the outer tubular shaft in which the inner tubular shaft is received can be joined to the handle only in a predefined rotational position relative thereto, so that when the outer tubular shaft is inserted into the slider, the outer tubular shaft automatically has the correct rotational orientation for joining the outer tubular shaft to the handle and to the aforesaid control elements.

In a further preferred embodiment, the actuation device has two sliders that are arranged in axially displaceable fashion on the handle, the one slider being joined to the outer tubular shaft and the other slider to the inner tubular shaft.

This feature is also advantageous, since with two sliders instead of one slider—the one slider serving to actuate the outer tubular shaft and the other slider to actuate the inner tubular shaft—a direct transfer of the axial motion of the respective slider to the outer tubular shaft or inner tubular shaft becomes possible.

It is further preferred in this context if the one slider is movable between the first or second position in order to axially displace the open clamping gripper, and if the other slider is movable between the second and third positions in order to displace the outer tubular shaft relative to the inner tubular shaft in order to close or open the clamping gripper.

As an alternative to this, it is preferred if the actuation device has a rotatable handle element, arranged on the handle, that can be rotated into the first, second, third, and optionally fourth position.

This embodiment of the actuation device also results in advantageously simple handling, with one-hand operation, of the screwdriver according to the present invention.

It is further preferred in this context if the rotatable handle element has internally located cams into which guide pins provided on the outer tubular shaft and inner tubular shaft engage, the cams being configured such that a rotation of the handle element is converted into an axial movement of the inner tubular shaft and outer tubular shaft, and a relative displacement between the inner tubular shaft and outer tubular shaft.

The advantage with this feature is that the cams can be configured directly in the rotatable handle element, with no need for additional parts for the purpose. Also preferred, instead of the actuation devices described above which have one or two axially movable sliders or a rotatable handle element, are actuation devices for the screwdriver according to the present invention that are displaceable between two or more positions of the actuation device, and rotatable between the remaining positions. An actuation device can be provided, for example, that is axially movable between the first and second positions, and is actuated from the second into the third position by a rotary movement.

In a further preferred embodiment, the inner tubular shaft is, at least in the third position, rotatable relative to the outer tubular shaft.

The further advantage of this feature is that the outer tubular shaft does not need to be rotated in the body as the screw is being screwed into or out of the bone, so that the rotation of the screwdriver does not traumatize tissue in the human body that is in contact with the outer tubular shaft.

In further preferred embodiment, the head of the shaft is replaceable.

The advantage of this feature is that one and the same screwdriver can be used for different types of screws having different screw heads.

Further advantages are evident from the description below and from the appended drawings.

It is understood that the features mentioned above and those yet to be explained below can be used not only in the respective combination indicated, but also in other combinations or in isolation, without leaving the context of the present invention.

BRIEF DESCRIPTION OF THE DRAWINGS

An exemplary embodiment of the invention is shown in the drawings and will be explained hereinafter in more detail with reference to the Figures, in which:

FIG. 6 shows a section along line VI—VI in FIG. 5;

FIG. 7 shows a front view of the slider of the actuation device of the screwdriver;

FIG. 8 shows a side view of one outer side of a control element of the actuation device;

FIG. 9 shows a side view of one inner side of the control element in FIG. 8;

FIG. 10 shows a side view, corresponding to FIG. 9, of a further control element of the actuation device.

DETAILED DESCRIPTION OF A PREFERRED EMBODIMENT

Figure 1:
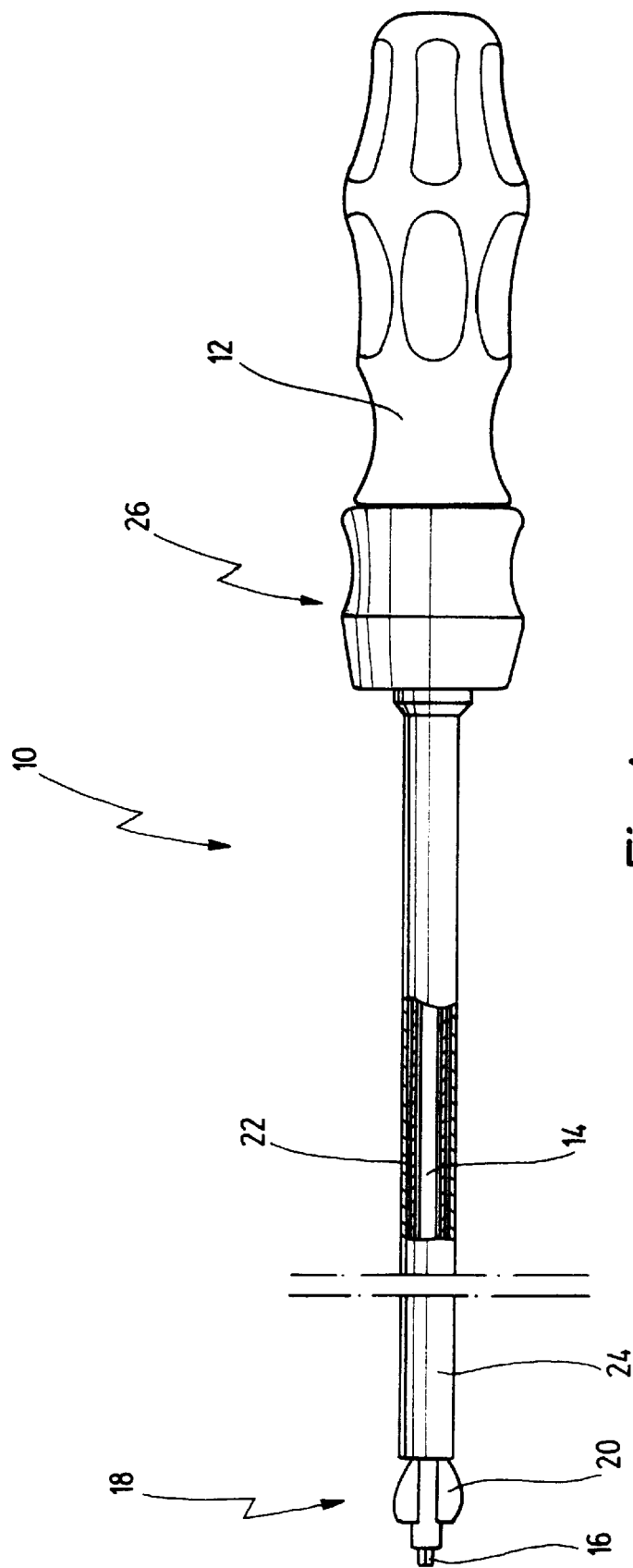
FIG. 1 shows a screwdriver in an overall representation, partially in longitudinal section along a longitudinal center plane of the screwdriver.

FIG. 1 shows a screwdriver labeled with the general reference character 10. Screwdriver 10 is used to introduce and screw a screw into the human and animal body, and to unscrew and remove a screw from the human or animal body.

Screwdriver 10 has at its rear end a handle 12. As is evident from FIG. 5, a shaft 14 is nonrotatably joined to handle 12, shaft 14 having at its distal end a head 16 that can be brought into engagement with a screw head of a screw in order to screw the screw in or out. Head 16 is mounted replaceably on shaft 14. Shaft 14 is elongated and has a length of approximately 40 to 50 cm.

Screwdriver 10 furthermore has a retention device 18 for retaining the screw on head 16. Retention device 18 has a clamping gripper 20 that is shown in FIG. 1 in its open position into which clamping gripper 20 is preloaded.

Clamping gripper 20 sits at the front end of an inner tubular shaft 22 that is arranged around shaft 14 and is axially displaceable thereon. Inner tubular shaft 22 extends approximately to handle 12, as will be described in further detail.

Retention device 18 further more has an outer tubular shaft 24 that is arranged around inner tubular shaft 22 and is axially displaceable both relative to inner tubular shaft 22 and together with it.

Screwdriver 10 also has an actuation device 26 for inner tubular shaft 22 and outer tubular shaft 24 which is arranged at the front end of handle 12. Actuation device 26 is also described later in more detail.

Inner tubular shaft 22 and outer tubular shaft 24 are removable from handle 12.

Figure 2:
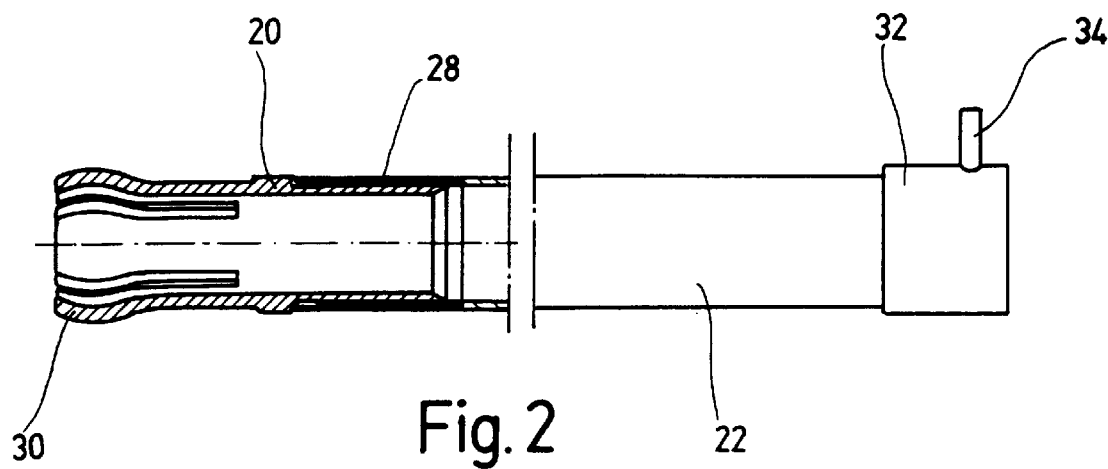
FIG. 2 shows the inner tubular shaft with clamping gripper in the state removed from the handle of the screwdriver, partially in longitudinal section.

In FIG. 2, inner tubular shaft 22 is shown in isolation. Clamping gripper 20 arranged at the front end of inner tubular shaft 22 is immovably joined via rear sleeve 28 to inner tubular shaft 22. At its front end, clamping gripper 20 has four tongues 30, arranged circumferentially with axial symmetry and separated from one another by axial slits, which can be radially elastically compressed and which automatically assume a radially spread position without external application of force. Clamping gripper 20 is thus preloaded into its open position.

A radially outwardly protruding pin 34 is immovably joined to end segment 32 on radially enlarged and segment 32 of inner tubular shaft 22.

Figure 3:
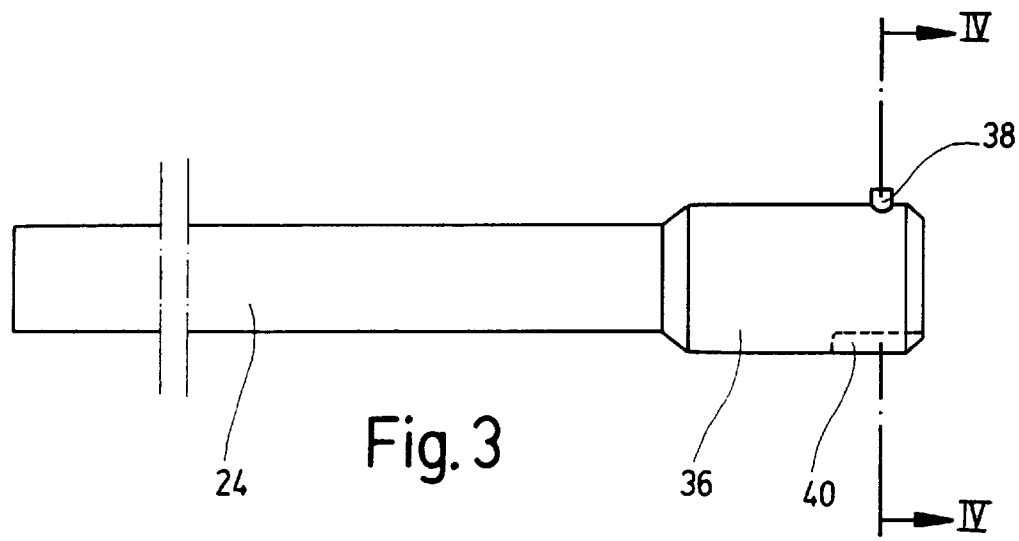
FIG. 3 shows the outer tubular shaft of the screwdriver in the sate removed from the handle of the screwdriver.
Figure 4:
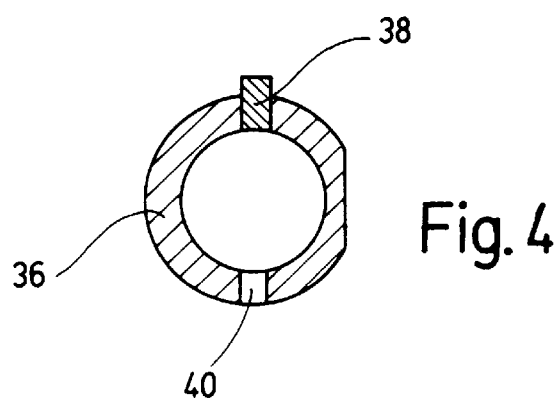
FIG. 4 shows a cross section through the outer tubular shaft along line IV—IV in FIG. 3.

In FIGS. 3 and 4, outer tubular shaft 24 is shown in isolation in the state removed from handle 12. A rear end segment 36 of outer tubular shaft 24 is radially enlarged. A radial pin 38 is immovably joined to end segment 36. Provided diametrically opposite pin 38 in end segment 36 is a cutout 40 of axially oblong configuration which serves to receive pin 34 of inner tubular shaft 22 when outer tubular shaft 24 is slid onto inner tubular shaft 22. Inner tubular shaft 22 can be inserted, with clamping ripper 20 at the front, into the rear end of outer tubular shaft 24 until the pin has completely entered recess 40 and comes to a stop against the front end thereof. The lengths of inner tubular shaft 22 and of outer tubular shaft 24 are coordinated with one another in such a way that when inner tubular shaft 22 and outer tubular shaft 24 are inserted into one another, tongues 30 project out of the front end of outer tubular shaft 24 just far enough that they can assume their open position. The outside diameter of the totality of tongues 30 in their opening position is slightly greater than the inside diameter of outer tubular shaft 24. When outer tubular shaft 24 is slid over tongues 30, they are thus compressed, thereby closing clamping gripper 20.

Figure 5:
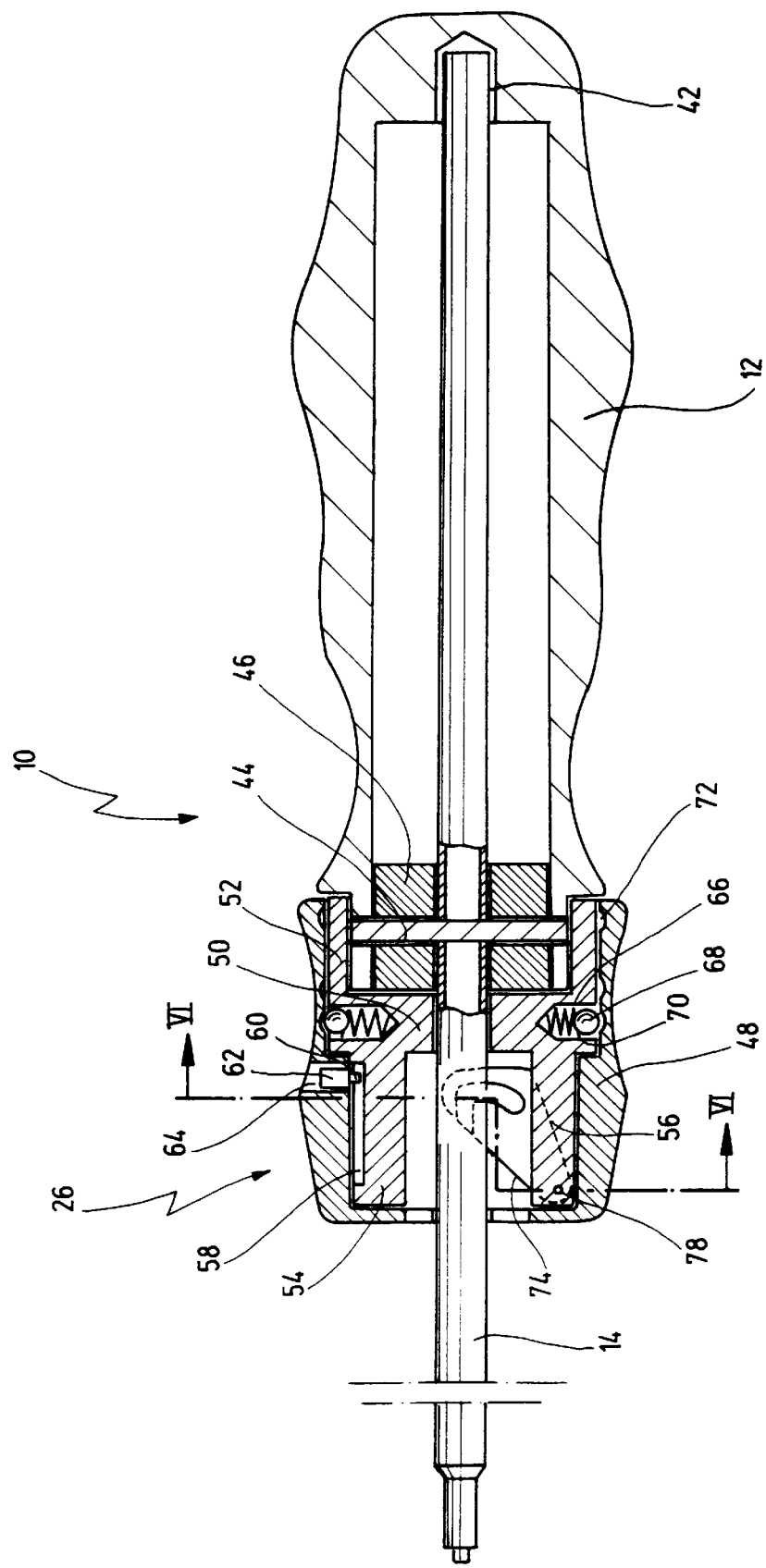
FIG. 5 shows a longitudinal section along a longitudinal center plane of the handle of the screwdriver, with the outer tubular shaft and inner tubular shaft removed.

In FIGS. 5 through 7, screwdriver 10 is shown with inner tubular shaft 22 and outer tubular shaft 24 removed. As is evident from FIG. 5, shaft 14 extends to the rear end of handle 12, where the rear end of shaft 14 is received in axially centered fashion in a blind hole 42 of handle 12 and is immovably joined to handle 12. A rotation prevention pin 44 passing diametrically through shaft 14 ensures that shaft 14 is joined axially and nonrotatably to handle 12. Rotation prevention pin 44 is additionally passed through a stable, nonrotatable centering ring 46.

Actuation device 26 has a slicer 48 that is arranged at the front end of handle 12 and is configured in the form of a sleeve. For that purpose, slider 48 is mounted in axially displaceable but nonrotatable fashion on a bearing element 50 that is immovably joined to handle 12 via a sleeve-like proximal end segment 52. At its front end, bearing element 50 has an axially extending first (upper, in FIGS. 5 and 6) flange 54 and a second (lower, in FIGS. 5 and 6) flange 56 also extending axially.

Configured in first flange 54 is a guide groove 58 in which a radial blunt tip 60 of a screw 62, which is screwed into a radial opening 64 in slider 48, is guided. Guide groove 58 is circumferentially delimited so that slider 48 is axially displaced on bearing element 50 but cannot be rotated. Provision can also be made for the guide groove not to be axially straight but rather to have a Z-shaped profile, so that slider 48 is only axially displaceable over a first segment of guide groove 58, is only rotatable over a second segment of guide groove 58, and is once again only axially displaceable over a third segment of guide groove 58. This can be used to create an interlock for slider 48, as will be explained later in more detail.

Radially incised blind holes 66, in each of which is received a ball 68 that is pushed radially outward by a spring 70, are provided in circumferentially distributed fashion in the middle segment of bearing element 50. Together with spherical-shell recesses 72 on the inner side of slider 48, balls 68 form ball catches; in the exemplary embodiment shown, three axial detent positions of slider 48 are provided in accordance with three axially spaced-apart shell-like recesses 72, corresponding, in conjunction with the operation of screwdriver 10, to specific positions of actuation device 26, as will be explained hereinafter in further detail.

Actuation device 26 furthermore has a first control element 74 for controlling the axial movement of outer tubular shaft 24; this is shown in FIG. 5 partially with dashed lines, since first control element 74 (as is evident from FIG. 6) is positioned alongside the longitudinal center axis of screwdriver 10. Also provided is a second control element 76 for controlling the axial movement of inner tubular shaft 22.

First control element 74 and second control element 76 are mounted on second flange 56, pivotably together about a common pivot axis 78; pivot axis 78 is constituted by a bearing pin 80 that penetrates through second flange 56 to each side and engages into a blind hole 82 of first control element 74 and into a blind hole 84 of second control element 76, and is immovably joined therein to first control element 74 and second control element 76.

First control element 74 is shown in isolation and at enlarged scale in FIGS. 8 and 9, while second control element 76 is shown in isolation in FIG. 10.

As shown in FIG. 8, a recess 88 of oblong configuration, into which (as shown in FIG. 6) a pin 90 screwed into slider 48 engages, is cut into an outer side 86 of first control element 74. A recess corresponding to recess 88, into which engages a pin 92 that is screwed into slider 48 opposite pin 90, is correspondingly provided on an outer side (not shown) of second control element 76. Upon axial displacement of slider 48 on bearing element 50, pins 90 and 92 cause a pivoting of first control element 74 and second control element 76 about pivot axis 78.

A cam in the form of a groove 96 is configured on an inner side 94 of first control element 74 (cf. FIG. 9). A cam in the form of a groove 100 is configured on an inner side 98 of second control element 76 (cf. FIG. 10), the cam represented by groove 100 differing in terms of its cam profile from the cam represented by groove 96.

Control element 74 with groove 96 serves to control the axial movement of outer tubular shaft 24; in the assembled state, pin 38 (cf. FIG. 6) of outer tubular shaft 24 engages into groove 96. Control element 76 with groove 100 correspondingly serves to control the axial movement of inner tubular shaft 22, in the assembled state, pin 34 of inner tubular shaft 22 (cf. FIG. 2) engages into groove 100.

Groove 96 furthermore has an open end 102, and groove 100 an open end 104, which allow the introduction of pins 34 and 38 into grooves 96 and 100, respectively, when inner tubular shaft 22 and outer tubular shaft 24 are assembled to the handle.

As shown in FIG. 7, one distal end face 106 of slider 48 has a non-round opening 107 adapted to end segment 36 of outer tubular shaft 24; additionally provided in end face 106 are diametrically opposite radial cutouts 108 and 110 through which pins 34 and 38 of inner tubular shaft 22 and outer tubular shaft 24, respectively, can be passed. As a result of the configuration of opening 107 of end face 106 and end segment 36 of outer tubular shaft 24, outer tubular shaft 24 can be introduced into slider 48, in order to join the outer tubular shaft and inner tubular shaft to handle 12, only in the rotational position defined by the opening of end face 106.

The assembly and disassembly of screwdriver 10, and the operation of screwdriver 10, will be described in more detail below with reference to FIG. 11. To illustrate the movement sequences, first control element 74 and second control element 76 have been shown detached from actuation device 74; for further elucidation, first actuation element 74 and second actuation element 76 are shown spaced apart from one another. It is understood, however, that first control element 74 and second control element 76 are attached to second flange 56 of bearing element 50 axially at the same height, and in the arrangement shown in FIGS. 5 and 6.

Figure 11:
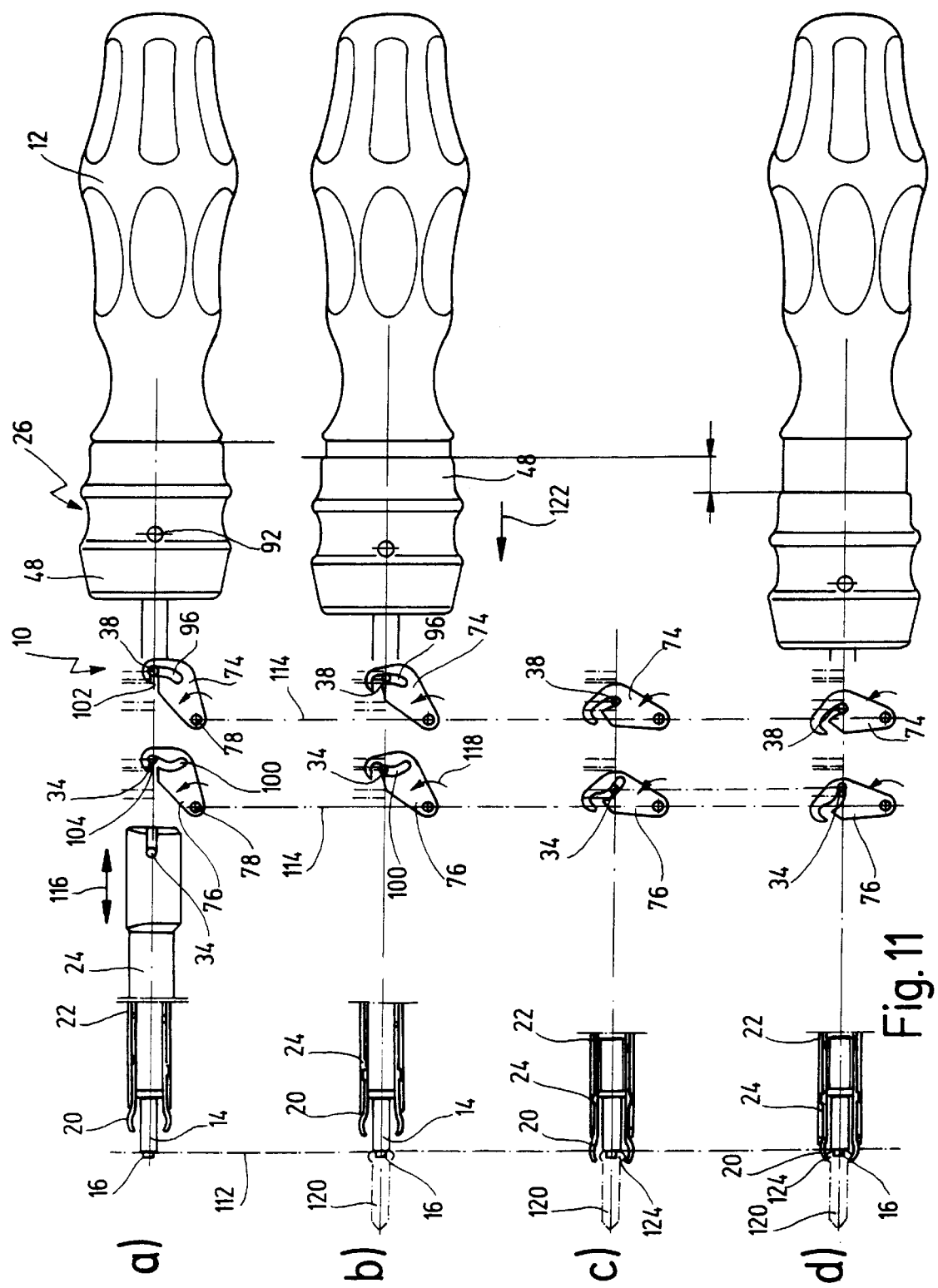
FIGS. 11 a) through 11 d) show schematic representations of the function of the screwdriver in four individual Figures.

In FIGS. 11 a) through 11 d), a dot-dash line 112 is drawn in as an axially stationary reference line indicating the axial position of immovable blade 16, and dot-dash line 114 is drawn in as a further axially stationary reference line, which is drawn twice because of the particular axially spaced-apart representation of first control element 74 and second control element 76, and reproduces the axially stationary position of pivot axis 78 of first control element 74 and of second control element 76.

Actuation device 26 and slider 48 have four positions, which are illustrated in FIGS. 11 a) through 11 d).

In FIG. 11 a), slider 48 is shown in the fourth position, in which slider 48 is pulled back into its maximally proximal location. With actuation device 26 in this position, inner tubular shaft 22 and outer tubular shaft 24 can be joined to handle 12 or removed from it, as indicated by a double arrow 116. In this fourth position of slider 48, which is also shown in FIG. 5, first control element 74 and second control element 76 are pivoted in the proximal direction about pivot axis 78, so that open end 102 of groove 96 of first control element 74, and open end 104 of groove 100 of second control element 76, face toward the distal end of screwdriver 10. In this position, pin 34 of inner tubular shaft 22 and pin 38 of outer tubular shaft 24 can move into and out of open ends 102 and 104, respectively. As shown in FIG. 5, a detent position of slider 48 is provided for this fourth position, i.e. the disassembly position of actuation device 26.

Pins 34 and 38 are automatically introduced by sliding inner tubular shaft 22 and outer tubular shaft 24 into slider 48 until a stop is felt.

Proceeding from the fourth position of actuation device 26, slider 48 is then displaced axially into the first position, which is shown in FIG. 11 b). Axial displacement of slider 48 out of the fourth position into the first position causes first control element 74 and second control element 76 to be pivoted about their common pivot axis 78 through a small angle in the direction of an arrow 118. Pin 34 of inner tubular shaft 22 and pin 38 of outer tubular shaft 24 are now, in this first position of actuation device 26, captured in groove 100 and groove 96, respectively, so that in this first position, inner tubular shaft 22 and outer tubular shaft 24 can no longer be pulled axially off handle 12 but rather are immovably joined to it.

As shown in FIG. 5, a detent position on slider 48 is also provided for the first position of actuation device 26. As slider 48 moves out of the fourth position into the first position, inner tubular shaft 22 and outer tubular shaft 24 perform a slight axial movement, as is evident from a comparison of the axial positions of pins 34 and 38 in FIG. 11 a) and FIG. 11 b).

With actuation device 26 in the first position, a screw 120 can now be placed onto head 16 of shaft 14. Despite the aforementioned slight axial movement of inner tubular shaft 22 and outer tubular shaft 24, clamping gripper 20 is still in a pulled-back position with respect to head 16, in which clamping gripper 20 does not impede the placement of screw 120.

By sliding slider 48 farther in the direction of an arrow 122 into a second position, first control element 74 and second control element 76 are pivoted further in the direction of arrow 118 until they have reached their rotational position shown in FIG. 11 c). As a result of the pivoting of first control element 74 and second control element 76, and because of the configuration of groove 100 and groove 96, pin 34 of inner tubular shaft 22 and pin 38 of outer tubular shaft 24 are together displaced axially in the distal direction, so that outer tubular shaft 24 and inner tubular shaft 22 are together moved axially. Clamping gripper 20 is thereby pushed, in the open state, over a screw head 124 of screw 120, as shown in FIG. 11 c).

In the exemplary embodiment shown, no detent position of slider 48 is provided for the second position of slider 48.

Further axial displacement of slider 48 in the direction of arrow 122 out of the second position in FIG. 11 c) into the third position shown in FIG. 11 d) now causes outer tubular shaft 24 to be displaced relative to inner tubular shaft 22, so that the distal end of outer tubular shaft 24 is pushed over clamping gripper 20 and compresses it into its closed position, so that screw head 124 of screw 120 is grasped by clamping gripper 20 and screw 120 is thus retained on head 16 in lossproof fashion and in axial alignment with the longitudinal axis of the screwdriver.

The relative motion between outer tubular shaft 24 and inner tubular shaft 22 is achieved by the fact that groove 100 of second control element 76, which serves to control inner tubular shaft 22, is configured such that second control element 76, as it pivots out of the rotational position shown in FIG. 11 c) into the rotational position shown in FIG. 11 d), does not axially displace pin 34 of inner tubular shaft 22 received in groove 100. Groove 96 of first control element 74, which serves to control outer tubular shaft 24, is configured, in contrast, such that as first control element 74 pivots out of the rotational position shown in FIG. 11 c) into the rotational position shown in FIG. 11 d), pin 38 is moved axially in the distal direction, thus resulting in the relative displacement between outer tubular shaft 24 and inner tubular shaft 22.

Once again, a detent position of slider 48 on bearing element 50, causing clamping gripper 20 to be immobilized in self-holding fashion in its closed position, is provided for the third position of slider 48 shown in FIG. 11 d).

Screw 120, which is now retained on head 16, can be introduced, using screwdriver 10, through an incision into the body and started at the desired target location, for example the spinal column, where screw 120 is to be screwed in. Screw 120 can now be screwed several turns into the bone by rotating handle 12, until screw 120 has experienced sufficient self-attachment in the bone. In order for screw 120 to be screwed completely into the bone, slider 48 is then pulled back in the opposite direction, out of the position shown in FIG. 11 c) into the first position shown in FIG. 11 b), causing clamping gripper 20 first to open and then to be pulled back behind screw head 124. Screw 120 can now be screwed completely into the bone until head 124 of screw 120 is countersunk.

It is understood that screwdriver 10 can be used correspondingly to unscrew and remove a screw from the human or animal body, for which purpose actuation device 26 is then operated accordingly, with no need for more detailed explanation at this juncture.

Slider 48 is particularly suitable for one-hand operation in which slider 48 is operated, for example, with the thumb and index finger of the same hand with which handle 12 is being held.

In order to enhance the operating reliability of screwdriver 10, provision can additionally be made for actuation device 26 to be capable of being moved from the first position shown in FIG. 11 b) into the first position shown in FIG. 11 a) only if the operator has first disengaged an interlock. An interlock of this kind can be configured in the form of an interlock that is releasable by way of a pushbutton, or, as already described above, by the fact that guide groove 56 of bearing element 50 has a Z-shaped configuration so that slider 48 can be moved from the first position into the fourth position only if slider 48 has first been rotated.

Provision can also be made, in the case of screwdriver 10, for outer tubular shaft 24 to be rotatable relative to shaft 14 and handle 12, so that outer tubular shaft 24 does not also rotate when screw 120 is screwed in or unscrewed.

What is claimed, is:

1. A screwdriver for introducing and screwing a screw into the human or animal body and/or for unscrewing and removing a screw from the human or animal body, comprising:
   a handle;
   a shaft connected to said handle, said shaft having a head at a front end of said shaft that can be brought into engagement with a screw head of a screw for screwing said screw in and out;
   a retention device for retaining said screw on said shaft, said retention device having an inner tubular shaft surrounding said shaft and having a clamping gripper at a front end of said inner tubular shaft, said clamping gripper being preloaded into an open position,
   said retention device further having an outer tubular shaft surrounding said inner tubular shaft;
   an actuation device for said inner tubular shaft and said outer tubular shaft, said actuation device being movable from a first position into a second position, as a result of which said clamping gripper is displaced over said head from a pulled-back position, and said actuation device being movable from said second position into a third position, as a result of which said outer tubular shaft is displaced relative to said inner tubular shaft over said clamping gripper in order to close the latter, and vice versa,
wherein
   at least one of said inner tubular shaft and said outer tubular shaft is joined removably to said handle,
   said actuation device is arranged on said handle and is movable into a fourth position in which said at least one of said inner tubular shaft and said outer tubular shaft is removable from said handle, and
   said at least one of said inner tubular shaft and said outer tubular shaft is fixed on said handle by moving said actuation device from said fourth position into said first position.

2. The screwdriver of claim 1, wherein said inner tubular shaft and said outer tubular shaft are together axially displaced by moving said actuation device between said first and said second position.

3. The screwdriver of claim 1, wherein said at least one of said inner tubular shaft and said outer tubular shaft is joined to said handle by a quick-release connection.

4. The screwdriver of claim 1, wherein said actuation device is movable into said fourth position only after an interlock has been disengaged.

5. The screwdriver of claim 4, wherein said interlock can be disengaged by way of a pushbutton.

6. The screwdriver of claim 1, wherein said actuation device is movable into said fourth position only after an interlock has been disengaged and said interlock can be disengaged by rotating said actuation device.

7. The screwdriver of claim 1, wherein said actuation device snaps into at least one of said first, second, third, and fourth position.

8. The screwdriver of claim 7, wherein said actuation device has ball catches for at least one of said first, second, third, and fourth position.

9. The screwdriver of claim 1, wherein said actuation device has at least one slider that is arranged in axially displaceable fashion on said handle.

10. The screwdriver of claim 9, wherein said slider is arranged at a front end of said handle.

11. The screwdriver of claim 1, wherein said actuation device has at least one slider that is arranged in axially displaceable fashion on said handle and said actuation device has at least one first control element that has on its inner side a groove configured as a cam into which a pin arranged at a rear end of said outer tubular shaft engages, said first control element being mounted on said handle pivotably about a pivot axis running perpendicular to a longitudinal direction of said shaft, and said slider having a pin that engages into a guide groove on an outer side of said first control element, so that by axial displacement of said slider, said control element is pivoted and said outer tubular shaft is thereby displaced.

12. The screwdriver of claim 1, wherein said actuation device has at lest one slider that is arranged in axially displaceable fashion on said handle and said actuation device has at least one second control element that has on its inner side a groove, configured as a cam, into which engages a pin arranged at a rear end of said inner tubular shaft, said second control element being mounted on said handle pivotably about a pivot axis running perpendicular to a longitudinal direction of said shaft, and said slider having a pin which engages into a guide groove on an outer side of said second control element so that by axial displacement of said slider, said second control element is pivoted and said inner tubular shaft is thereby displaced.

13. The screwdriver of claim 12, wherein said groove of said first control element and said groove of said second control element are open at their front ends, and a pin of said outer tubular shaft and a pin of said inner tubular shaft can enter said groove and emerge from it axially when said actuation device is in its fourth position, and said pin of said inner tubular shaft and said pin of said outer tubular shaft are captured in said groove as soon as said actuation device has been moved into said first position.

14. The screwdriver of claim 1, wherein said actuation device has at least one slider that is arranged in axially displaceable fashion on said handle and a front end face of said slider has a non-round opening through which said outer tubular shaft is passed, a rear end segment of said outer tubular shaft having a corresponding complementary peripheral shape.

15. The screwdriver of claim 1, wherein said actuation device has two sliders that are arranged in axially displaceable fashion on said handle, said one slider being joined to said outer tubular shaft and said other slider to said inner tubular shaft.

16. The screwdriver of claim 15, wherein said one slider is movable between said first and said second position in order to axially displace said open clamping gripper, and said other slider is movable between said second and said third position in order to displace said outer tubular shaft relative to said inner tubular shaft in order to close or open said clamping gripper.

17. The screwdriver of claim 1, wherein said actuation device has a rotatable handle element, arranged on said handle, that can be rotated into said first, second, third, and fourth position.

18. The screwdriver of claim 17, wherein said rotatable handle element has internally located cams into which guide pins provided on said outer tubular shaft and said inner tubular shaft engage, said cams being configured such that a rotation of said handle element is converted into an axial movement of said inner tubular shaft and said outer tubular shaft, and a relative displacement between said inner tubular shaft and said outer tubular shaft.

19. The screwdriver of claim 1, wherein said inner tubular shaft is, at least in said third position of said actuation device, rotatable relative to said outer tubular shaft.

20. The screwdriver of claim 1, wherein said head of said shaft is replaceable.

* * * * *